(12) United States Patent
Ters et al.

(10) Patent No.: US 9,051,257 B2
(45) Date of Patent: Jun. 9, 2015

(54) METHOD OF OBTAINING ACETATE FROM LIGNOCELLULOSE SPECIFICATION IDENTIFICATION

(75) Inventors: Thomas Ters, Vienna (AT); Karin Fackler, Vienna (AT); Kurt Messner, Vienna (AT); Ortwin Ertl, Vasoldsberg (AT)

(73) Assignee: ANNIKKI GMBH, Graz (AT)

( * ) Notice: Subject to any disclaimer, the term of this patent is extended or adjusted under 35 U.S.C. 154(b) by 0 days.

(21) Appl. No.: 14/349,176

(22) PCT Filed: Sep. 5, 2012

(86) PCT No.: PCT/EP2012/067314
§ 371 (c)(1),
(2), (4) Date: May 19, 2014

(87) PCT Pub. No.: WO2013/050210
PCT Pub. Date: Apr. 11, 2013

(65) Prior Publication Data
US 2014/0316158 A1      Oct. 23, 2014

(30) Foreign Application Priority Data
Oct. 5, 2011 (AT) ................ A 1443/2011

(51) Int. Cl.
*C07C 51/41*        (2006.01)
*C07G 1/00*         (2011.01)

(52) U.S. Cl.
CPC . *C07C 51/41* (2013.01); *C07G 1/00* (2013.01); *C07C 51/412* (2013.01)

(58) Field of Classification Search
CPC .................................................. C07C 51/41
USPC ........................................................ 562/515
See application file for complete search history.

(56) References Cited

U.S. PATENT DOCUMENTS

| 1,695,742 | A |   | 12/1928 | Rawling |         |
|-----------|---|---|---------|---------|---------|
| 4,395,543 | A |   | 7/1983  | Wang et al. |     |
| 5,264,623 | A |   | 11/1993 | Oehr et al. |     |
| 5,705,216 | A | * | 1/1998  | Tyson   | 426/478 |
| 8,309,694 | B2| * | 11/2012 | Belanger et al. | 530/507 |
| 2009/0305374 | A1 |   | 12/2009 | Retsina et al. | |

FOREIGN PATENT DOCUMENTS

| WO | WO 2007111605 A1 | 10/2007 |
| WO | WO 2011014894 A2 | 2/2011  |

OTHER PUBLICATIONS

International Preliminary Report on Patentability for International Application No. PCT/EP2012/067314 dated Apr. 18, 2014 (8 pgs).

* cited by examiner

*Primary Examiner* — Shailendra Kumar
(74) *Attorney, Agent, or Firm* — Workman Nydegger

(57) ABSTRACT

A method of obtaining an aqueous solution of an alkali acetate from lignocellulose, wherein lignocellulose is treated with a first aqueous extraction solution having a pH value in the range of 12 to 14 and a content of a $C_{1-4}$ alcohol, in particular ethanol or isopropanol, in the range of 40% to 90%, in particular of from 75% to 85%, whereby a first aqueous solution of an alkali acetate is obtained, and wherein said first solution of an alkali acetate is used to treat additional lignocellulose in order to enrich additional acetate in said first solution.

12 Claims, 2 Drawing Sheets

METHOD OF OBTAINING ACETATE FROM LIGNOCELLULOSE SPECIFICATION IDENTIFICATION

This application is a 371 of PCT/EP2012/067314, filed on Sep. 5, 2012.

The invention relates to a method of obtaining an aqueous solution of an alkali acetate from lignocellulose.

In connection with the shortage of crude oil, the renewable raw material lignocellulose (straw, wood, paper waste, etc.) is becoming more and more important as a starting material for chemical products and fuels. Lignocellulose consists of the ultrastructurally cross-linked polymeric main components cellulose, hemicellulose and lignin, which often constitute about 85-90% of the raw material. The remainder may be summarized under the term "low-molecular ingredients". Among those ingredients, particularly the acetate is noteworthy besides the extractives and inorganic escort substances. Acetyl groups occur mainly in hardwoods and grasses and other lignocelluloses. Therein, they are chemically bound, in most cases, to the hemicellulose, more concretely in the polymer O-acetyl-4-O-methylglucurono-(arabino)xylan. The acetate is of major importance in several respects. As a valuable substance, it may be extracted in the form of acetic acid from pulp cooking liquors of hardwood pulps via distillation. In the production of bioalcohol from lignocellulosic substrates such as, e.g., straw, acetate is a strong inhibitor, which negatively affects the alcohol yield.

The cleavage of the components present as polymers and their fractionation into individual product streams as well as their further processing into higher-value products is the task of biorefineries of a biochemical platform. The profitability of such biorefineries depends largely on which added value can be drawn from the product streams. This is, in turn, heavily influenced by the purity of the individual product streams, since downstream fractionation processes can be difficult and costly. Hence, a process in which the cleavage of the individual main components occurs as selectively as possible may be considered as ideal. For this purpose, it is advantageous to place the step of extracting the extractives at the start of biorefinery methods.

In addition to the use of the carbohydrate proportion, the amount and quality of the obtained lignin has a strong influence on the added value of the entire process. Lignin is gaining very much economical importance as a substitute for petrochemically produced aromates. In turn, the possible uses of the obtained lignin depend very much on the chemical composition thereof, most notably, however, on the molecular weight of the obtained lignin fraction. In particular, sulfur-free, low-molecular lignin fractions are in demand as raw materials for applications in the manufacture of plastics and resins. In contrast to Kraft or sulfite pulp mills, biorefineries are designed to produce sulfur-free lignin.

Among the methods for the degradation of lignocellulose as applied in biorefineries, in particular alkaline methods are to be pointed out, the degradation principle of which is primarily the removal of lignin. The underlying chemical principle is alkaline saponification, whereby both the connection between lignin and hemicellulose and the acetic acid-hemicellulose esters are cleaved. Such a method is described in U.S. Pat. No. 4,395,543, Avgerinos and Wang (1981). A method for the degradation of lignocellulose is described in which an extraction solution consisting of water, between 40 and 75% of alcohol and a pH of between 11 and 14 is used. In addition, it is evident from the patent that the amount of released lignin reduces virtually to zero if the ethanol concentration is increased to up to 100%. Furthermore, it is described that also the amount of released sugars reduces to virtually zero if the alcohol concentration is raised to 100%. The progression of the release of acetate is not described.

In the present patent application, it is shown that, in case that certain reaction conditions are chosen, primarily in case that the correct alcohol concentration is chosen in an aqueous alkaline solution, acetate may be obtained from straw surprisingly almost quantitatively.

The present invention provides a method of obtaining an aqueous solution of an alkali acetate from lignocellulose, wherein lignocellulose is treated with a first aqueous extraction solution having a pH value in the range of 12 to 14 and a content of a $C_{1-4}$ alcohol, in particular ethanol or isopropanol, in the range of 40% to 90%, in particular of 75% to 85%, whereby a first aqueous solution of an alkali acetate is obtained, and wherein said first solution of an alkali acetate is used to treat additional lignocellulose in order to enrich additional acetate in said first solution.

A method provided by the present invention is designated herein also as "method according to (of) the present invention".

In a method according to the present invention, as lignocellulose in particular hardwood, straw, bagasse or annual and perennial grasses have proved to be advantageous.

One advantage of a method according to the present invention is the high acetate concentration which is achievable in this way and, and as a result of this, the easier separation of the acetate.

A further advantage is the decrease of consumption of acetate extraction solution, which is associated therewith.

A further advantage is the separation of acetate and lignin in a large extent, which otherwise would accumulate jointly in a solution.

A further advantage is the fact that, for recycling the LIGNIN solution, less NaOH needs to be added, since less acetate is in solution.

A further advantage is the fact that, due to the reduced demand for caustic solution (NaOH), fewer salts accumulate.

A further advantage is that the LIGNIN solution can thereby be used on new amounts of straw and, as a result, also the concentration of lignin in solution can be increased, or, respectively, the amount of solvents which is required in relation to the straw can be reduced.

Another advantage is that further lignin extraction steps are not hampered by the presence of acetate.

Another advantage is that, after a further lignin extraction step, acetate does not have to be removed separately.

In a method according to the present invention, acetate may be extracted surprisingly from wheat straw in high yields already after 30 minutes at a temperature of 70° C. and a pH value in the range of 12 to 14 and with an alcohol content in the range of 40% to 90%. If the alcohol content is raised to above 85% under those conditions, the amount of the extracted acetate decreases.

It has been found that, in a method according to the present invention, an ethanol concentration of 80% can be considered as optimal for the extraction of acetate from straw, since, with 80% ethanol, the amount of released sugars is very low as well and a high selectivity of the acetate production can be achieved.

Furthermore, it has been shown that, with 80% ethanol, 16% of the lignin is released already after 30 minutes under the above-mentioned conditions. Surprisingly, it has become apparent that the obtained lignin has a very low molecular weight (Mw 1340, Mn 850) with a very narrow molecular weight distribution (Pd 1.58).

In a method according to the present invention, it is thus shown that, under the optimal conditions as described, it is surprisingly possible to obtain acetate quantitatively and, simultaneously, 16% very low-molecular lignin from straw.

Furthermore, it has been found according to the present invention that the extracted components acetate and lignin can be concentrated by repeated recycling of the extraction solution onto a—in each case fresh—lignocellulose substrate under metering spent basic solution, such as sodium hydroxide. As shown in Example 4, surprisingly the amounts of both the acetate and the lignin increase linearly in the recycling solution with the recycling steps and do not follow a saturation curve, as might have been expected. After 7 cycles, the acetate content could be increased from 0.94 mg/ml to 6.42 mg/ml, and the lignin content could be increased from 1.88 mg/ml to 13.67 mg/ml. The number of extraction cycles may be chosen freely depending on the desired final concentration of the extractives, or can be performed for example until saturation takes place.

As is evident from Example 5, the extraction can be carried out also at room temperature with a prolonged reaction time, and results in similar results as at 70° C. (see Example 4).

As a result of the successful concentration, a final concentration is achieved which even renders the separation of the acetate and of the low-molecular lignin economically sustainable. Furthermore, the amount of alcohol to be used, based on the total amount of treated biomass is drastically reduced by the recycling.

With the following examples, preferred embodiments of the invention are described in more detail.

EXAMPLE 1

Figure 1:
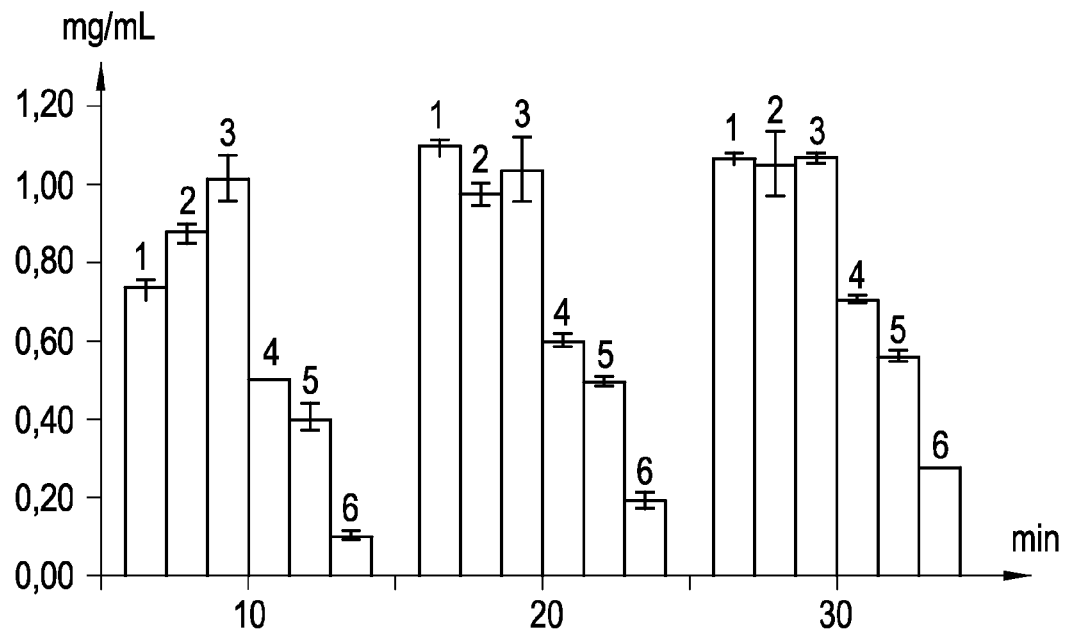
FIG. 1 shows the time course (in minutes) of the acetate concentration (mg/mL) in the extraction solution at 70° C. and with different ethanol contents (EtOH), wherein (1) denotes 40% EtOH, (2) denotes 60% EtOH, (3) denotes 80% EtOH, (4) denotes 90% EtOH, (5) denotes 95% EtOH and (6) denotes 100% EtOH in the extraction solution.

Time Course of the Acetate Concentration in the Extraction Solution at 70° C. and with Different Ethanol Contents 10 g of shredded wheat straw were suspended in a 500 mL reaction vessel in 200 mL (5% solids content) of a solution preheated to 70° C. and consisting of water/ethanol at different ratios (40%, 60%, 80%, 90%, 95%, 100% EtOH) and 0.8 g of NaOH. The suspension was continuously stirred magnetically at 200 rpm and 70° C. for 10, 20 or 30 minutes. Thereupon, the solids content was separated by filtration, and the acetate content of the solution was determined enzymatically. As can be seen in FIG. 1, most of the acetyl groups are hydrolyzed in the investigated time period at ethanol concentrations ranging between 60% and 80%.

EXAMPLE 2

Amounts of the Extracted Lignin With Different Ethanol Contents 10 g of shredded wheat straw were suspended in a 500 mL reaction vessel in 200 mL (5% solids content) of a solution preheated to 70° C. and consisting of water/ethanol at different ratios (40%, 60%, 80%, 90%, 95%, 100% EtOH) and 0.8 g of NaOH. The suspension was continuously stirred magnetically at 200 rpm and 70° C. for 24 hours. Thereupon, the solids content was separated by filtration. The lignin content in the solution was determined photometrically at 280 nm.

TABLE 1

Amounts of the extracted lignin with different ethanol contents

| | |
|---|---|
| 40% ethanol | 80% |
| 60% ethanol | 75% |
| 80% ethanol | 25% |
| 100% ethanol | 5% |

EXAMPLE 3

Determination of the Molecular Weight of a Lignin Solution Obtained With 80% Ethanol 10 g of shredded wheat straw were suspended in a 500 mL reaction vessel in 200 mL (5% solids content) of a solution preheated to 70° C. and consisting of 20% of water, 80% of ethanol and 0.8 g of NaOH. The suspension was continuously stirred magnetically at 200 rpm and 70° C. for 30 minutes. Thereupon, the solids content was separated by filtration. The average molecular weight of the lignin extracted with 80% ethanol was analyzed by means of an alkaline HPSEC system (Tosoh Bioscience TSK PW 5000-3000).

TABLE 2

($M_w$ weight average, $M_n$ number average, $P_d$ polydispersity):

| | |
|---|---|
| $M_w$ | 1340 |
| $M_n$ | 850 |
| $P_d$ | 1.58 |

EXAMPLE 4

Recycling to the Extraction Stage for Obtaining Acetate and Lignin, Respectively 10 g of shredded wheat straw were suspended in a 500 mL reaction vessel in 200 mL (5% solids content) of a solution consisting of 20% of water, 80% of ethanol and 0.8 g of NaOH. The suspension was continuously stirred magnetically at 200 rpm and 70° C. for 30 minutes. After the extraction, the solution was separated from the solid by filtration, adjusted to the initial pH value with fresh NaOH, and fresh straw (5% w/v) was added.

The suspension was again treated under the conditions as described above and subjected to a further recycling step after the separation of the solids.

Figure 2:
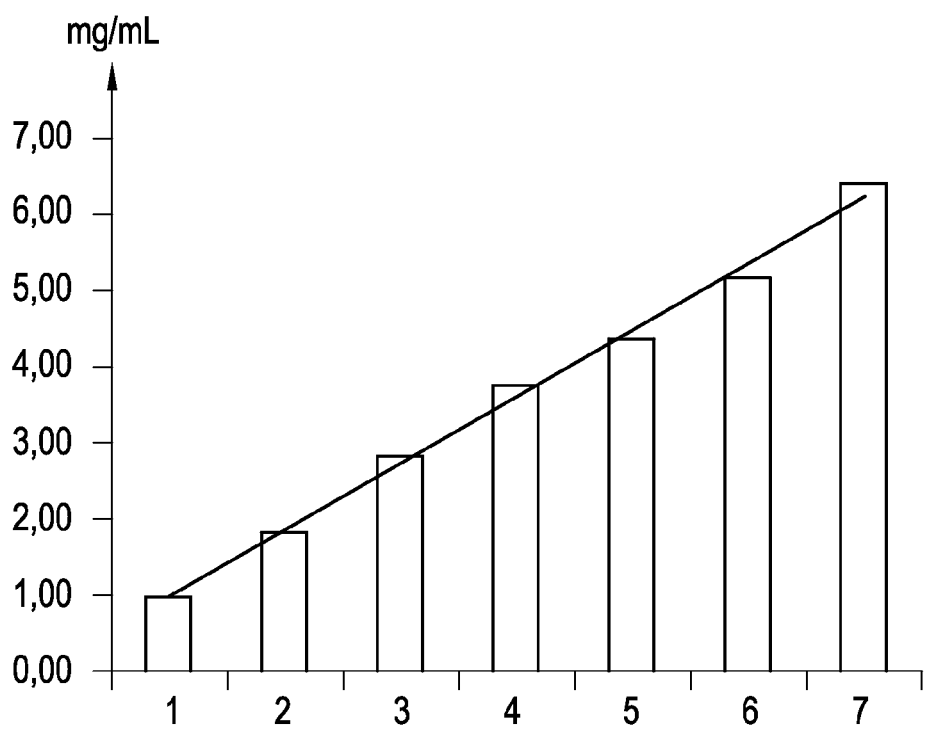
FIG. 2 shows the increase of the acetate content (mg/mL) in the extraction solution if the solution is being recycled. The increase across 7 cycles is virtually linear.
Figure 3:
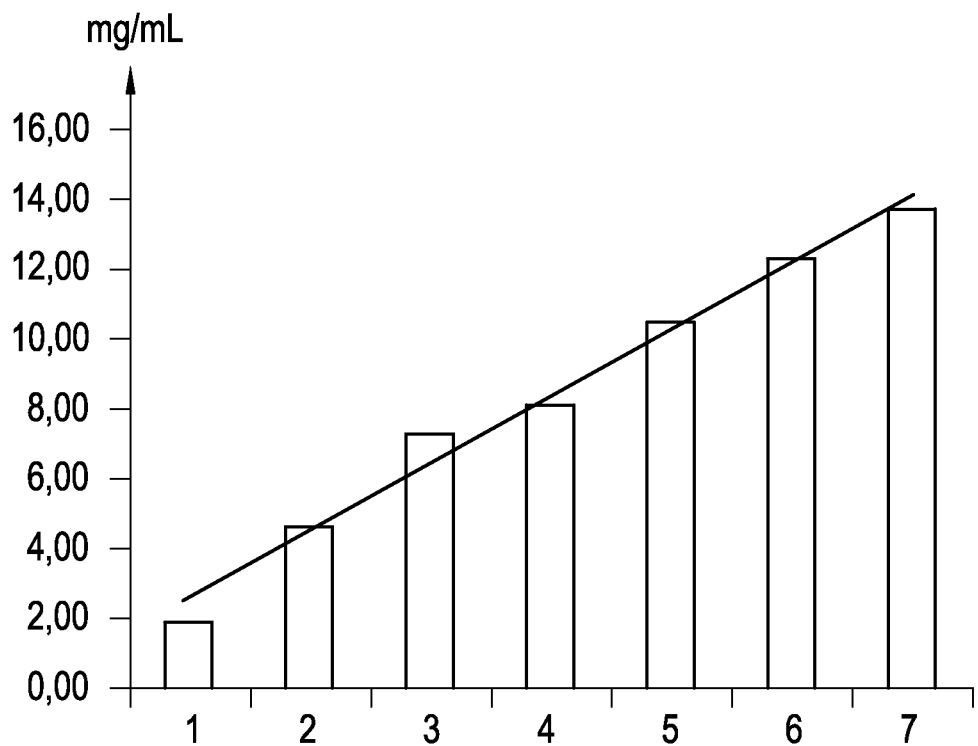
FIG. 3 shows the increase in the lignin content (mg/mL) in the extraction solution if the solution is being recycled. The increase across 7 cycles is virtually linear.

Before each recycling step, a sample was taken, and the lignin content as well as the acetate content of the solution were determined As can be seen from FIG. 2 and FIG. 3, both the lignin concentration and the acetate concentration rise linearly in the solution with each recycling step.

From the solid, which was fresh in each case, 0.91 mg/mL of acetate and 1.97 mg/mL of lignin on average were removed per extraction step. Deviations from those values may be explained by the variability of the extraction material.

EXAMPLE 5

Time Course of the Acetate Concentration in the Extraction Solution at 25° C.

Figure 4:
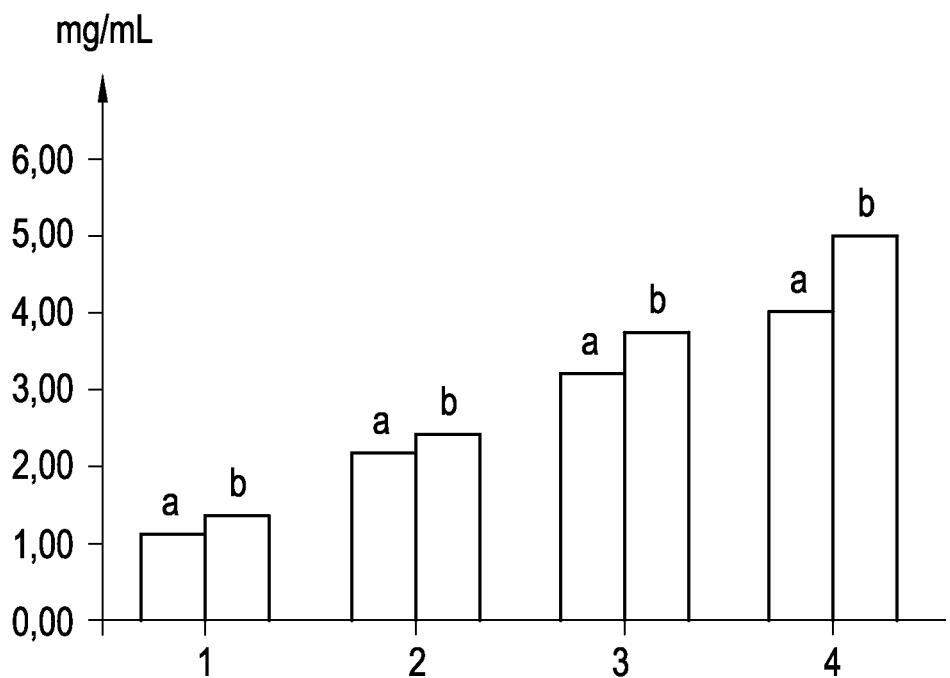
FIG. 4 shows the acetate content (a) and the lignin content (b) in mg/mL after the respective recycling of the extraction solution at room temperature (25° C.) in cycles 1 to 4.

10 g of shredded wheat straw was suspended in a 500 mL reaction vessel in 200 mL (5% solids content) of a solution consisting of 20% of water, 80% of ethanol and 0.8 g of NaOH. The suspension was continuously stirred magnetically at 200 rpm and 25° C. for 16 hours. After the extraction, the solution was separated from the solid by filtration, adjusted to the initial pH value with fresh NaOH, and fresh straw (5% w/v) was added. The suspension was again treated under the conditions as described above and subjected to a further recycling step after the separation of the solid. Before each recycling step, a sample was taken, and the lignin content as well as the acetate content of the solution were determined The (linear) increase of the acetate and lignin contents in the extraction solution, if the solution is being recycled in 4 cycles, is shown in FIG. 4.

The invention claimed is:

1. A method of obtaining an aqueous solution of an alkali acetate from lignocellulose, comprising:

treating lignocellulose with a first aqueous extraction solution having a pH value in the range of 12 to 14 and a content of a $C_{1-4}$ alcohol in the range of 40% to 90% and obtaining a first aqueous solution of an alkali acetate, and treating additional lignocellulose with said first solution of an alkali acetate in order to enrich additional acetate in said first solution.

2. A method according to claim 1, wherein the $C_{1-4}$ alcohol is ethanol.

3. A method according to claim 1, wherein the $C_{1-4}$ alcohol is isopropanol.

4. A method according to claim 1, wherein the content of a $C_{1-4}$ alcohol is in the range of 75% to 85%.

5. A method according to claim 1, characterized in that as lignocellulose hardwood, straw, bagasse or annual and/or perennial grasses are used.

6. A method according to claim 2, wherein the content of a $C_{1-4}$ alcohol is in the range of 75% to 85%.

7. A method according to claim 3, wherein the content of a $C_{1-4}$ alcohol is in the range of 75% to 85%.

8. A method according to claim 2, characterized in that as lignocellulose hardwood, straw, bagasse or annual and/or perennial grasses are used.

9. A method according to claim 3, characterized in that as lignocellulose hardwood, straw, bagasse or annual and/or perennial grasses are used.

10. A method according to claim 4, characterized in that as lignocellulose hardwood, straw, bagasse or annual and/or perennial grasses are used.

11. A method according to claim 6, characterized in that as lignocellulose hardwood, straw, bagasse or annual and/or perennial grasses are used.

12. A method according to claim 7, characterized in that as lignocellulose hardwood, straw, bagasse or annual and/or perennial grasses are used.

* * * * *